United States Patent
Zaslavsky et al.

(10) Patent No.: US 9,002,435 B2
(45) Date of Patent: Apr. 7, 2015

(54) SYSTEM AND METHOD FOR INTEGRATING ELECTROMAGNETIC MICROSENSORS IN GUIDEWIRES

(75) Inventors: Ella Zaslavsky, Marblehead, MA (US); Samuel Joseph Akins, Tewksbury, MA (US)

(73) Assignee: General Electric Company, Schenectady, NY (US)

( * ) Notice: Subject to any disclaimer, the term of this patent is extended or adjusted under 35 U.S.C. 154(b) by 1322 days.

(21) Appl. No.: 12/165,636

(22) Filed: Jun. 30, 2008

(65) Prior Publication Data

US 2009/0326368 A1  Dec. 31, 2009

(51) Int. Cl.
- A61B 5/05 (2006.01)
- A61M 25/00 (2006.01)
- A61M 25/09 (2006.01)
- A61B 5/06 (2006.01)
- A61B 19/00 (2006.01)
- A61B 17/22 (2006.01)

(52) U.S. Cl.
CPC ...... *A61M 25/09* (2013.01); *A61B 5/05* (2013.01); *A61M 25/00* (2013.01); *A61B 5/06* (2013.01); *A61B 19/5244* (2013.01); *A61B 2017/22042* (2013.01); *A61B 2019/5251* (2013.01); *A61M 2025/09091* (2013.01); *A61M 2025/09108* (2013.01); *A61M 2025/09175* (2013.01)

(58) Field of Classification Search
CPC ............ A61B 2017/22042; A61B 2019/5251; A61B 5/06; A61B 5/05; A61B 19/5244; A61M 2025/09091; A61M 25/09; A61M 2025/09175; A61M 25/00; A61M 2025/09108

USPC .......................................... 600/422–424, 585
See application file for complete search history.

(56) References Cited

U.S. PATENT DOCUMENTS

| | | | |
|---|---|---|---|
| 4,173,228 | A | 11/1979 | Van Steenwyk et al. |
| 4,572,198 | A | 2/1986 | Codrington |
| 4,719,924 | A | 1/1988 | Crittenden et al. |
| 4,763,647 | A | 8/1988 | Gambale |
| 4,832,047 | A | 5/1989 | Sepetka |
| 4,905,698 | A | 3/1990 | Strohl et al. |
| 5,386,828 | A | 2/1995 | Owens et al. |
| 5,395,332 | A | 3/1995 | Ressemann et al. |
| 5,402,799 | A | 4/1995 | Colon et al. |
| 5,406,960 | A | 4/1995 | Corso |
| 5,437,277 | A | 8/1995 | Dumoulin et al. |
| 5,497,786 | A | 3/1996 | Urick |
| 5,569,196 | A | 10/1996 | Muni et al. |
| 5,592,939 | A | 1/1997 | Martinelli |
| 5,727,553 | A | 3/1998 | Saad |
| 5,876,386 | A | 3/1999 | Samson |
| 5,897,819 | A | 4/1999 | Miyata et al. |
| 5,938,623 | A | 8/1999 | Quiachon et al. |
| 5,947,940 | A * | 9/1999 | Beisel .......................... 604/526 |
| 6,104,944 | A * | 8/2000 | Martinelli .................... 600/424 |
| 6,226,547 | B1 | 5/2001 | Lockhart et al. |
| 6,233,476 | B1 | 5/2001 | Strommer et al. |

(Continued)

FOREIGN PATENT DOCUMENTS

WO  WO03086498  10/2003

*Primary Examiner* — Vani Gupta
(74) *Attorney, Agent, or Firm* — Kenneth E. Horton; Kirton McConkie

(57) ABSTRACT

A system and method of integrating electromagnetic microsensors into interventional endovascular devices such as guidewires for tracking guidewires within vessels of a body with the use of a surgical navigation system.

28 Claims, 8 Drawing Sheets

(56) References Cited

U.S. PATENT DOCUMENTS

| | | | |
|---|---|---|---|
| 6,461,370 B1 | 10/2002 | Gray et al. | |
| 6,544,041 B1 * | 4/2003 | Damadian | 434/262 |
| 6,615,155 B2 | 9/2003 | Gilboa | |
| 6,783,536 B2 | 8/2004 | Vilsmeier et al. | |
| 6,785,571 B2 | 8/2004 | Glossop | |
| 6,833,814 B2 | 12/2004 | Gilboa et al. | |
| 6,947,788 B2 | 9/2005 | Gilboa et al. | |
| 7,025,758 B2 | 4/2006 | Klint | |
| 7,169,161 B2 | 1/2007 | Bonnette et al. | |
| 7,499,756 B2 * | 3/2009 | Bowe et al. | 607/119 |
| 7,532,920 B1 * | 5/2009 | Ainsworth et al. | 600/342 |
| 7,674,253 B2 * | 3/2010 | Fisher et al. | 604/528 |
| 8,239,003 B2 * | 8/2012 | Akins | 600/424 |
| 2002/0042571 A1 * | 4/2002 | Gilboa et al. | 600/429 |
| 2002/0043118 A1 | 4/2002 | Claude | |
| 2002/0198676 A1 | 12/2002 | Kirsch et al. | |
| 2004/0019447 A1 | 1/2004 | Shachar | |
| 2004/0097804 A1 | 5/2004 | Sobe | |
| 2004/0181174 A2 | 9/2004 | Davis et al. | |
| 2005/0182319 A1 | 8/2005 | Glossop | |
| 2005/0240147 A1 | 10/2005 | Makower et al. | |
| 2005/0283067 A1 | 12/2005 | Sobe | |
| 2006/0173291 A1 | 8/2006 | Glossop | |
| 2006/0241519 A1 | 10/2006 | Hojeibane et al. | |
| 2007/0027524 A1 | 2/2007 | Johnson et al. | |
| 2007/0055128 A1 | 3/2007 | Glossop | |
| 2007/0208251 A1 | 9/2007 | Anderson et al. | |
| 2007/0208252 A1 * | 9/2007 | Makower | 600/424 |

* cited by examiner

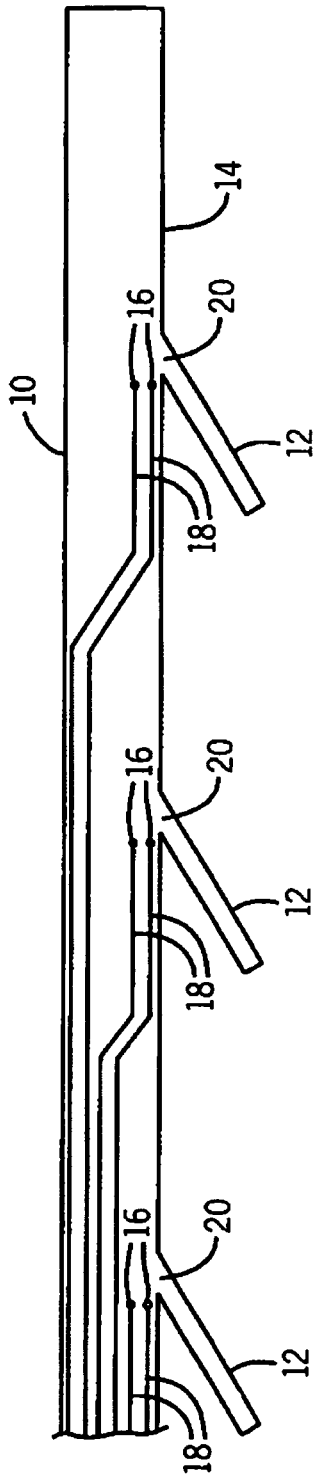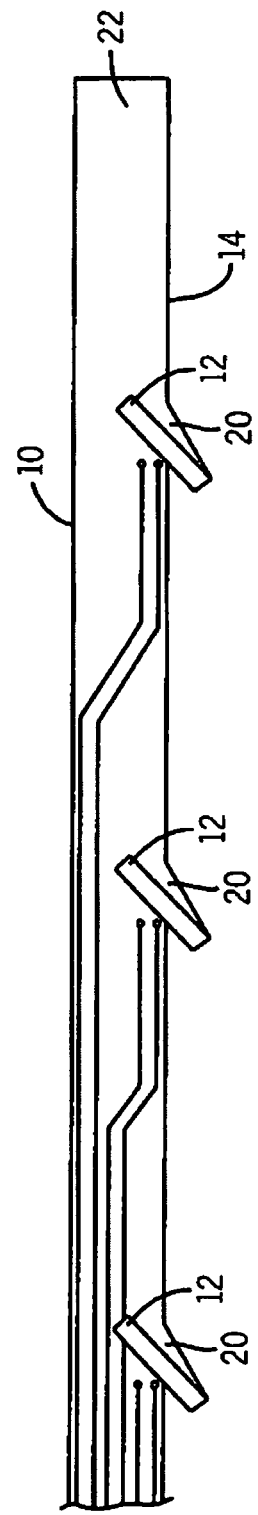

SYSTEM AND METHOD FOR INTEGRATING ELECTROMAGNETIC MICROSENSORS IN GUIDEWIRES

BACKGROUND OF THE INVENTION

This disclosure relates generally to guidewires, and more particularly, to a system and method of integrating trackable devices into guidewires for tracking the guidewires within vasculature of a body.

A guidewire typically includes a flexible wire to be positioned in an organ, vessel, or duct of a body for the purpose of directing passage of a larger device threaded over or along the length of the guidewire to a desired location in the vasculature of a body. A wide variety of guidewires have been developed for various applications including medical applications. Generally, guidewires are used to aid in the insertion of catheters or other devices into a body. During endovascular interventions, a guidewire is inserted into a body system such as the vascular system at a point of entry, which is usually a small percutaneous incision in the arm, leg or groin, and advanced to a desired location, typically under fluoroscopic guidance. Accurate positioning of the guidewire with respect to the vasculature is generally required for a successful procedure.

In some applications, a generally hollow cylindrical catheter is slipped over the guidewire and directed to the desired location by following the guidewire. The catheter doesn't have the stiffness or rigidity of the guidewire. The guidewire and catheter must be precisely and efficiently positioned at the desired location in order to most effectively treat the underlying medical condition.

There are clinical benefits to tracking the tip, a portion or entire length of a guidewire that is used in endovascular interventional applications. One benefit is that a user can more efficiently navigate a guidewire to a target site with the aid of a surgical navigation tracking system. Another benefit is that the tracking system will provide real-time location data of the guidewire to the user, requiring a lower radiation dose from the imaging apparatus.

Guidewires have been developed to include one or more trackable devices, such as microsensors, integrated within the guidewire. Surgical navigation systems may then be employed to track the tip, a portion or entire length of the guidewire by tracking the position and orientation of integrated microsensors, for example. A clinician may use the position and orientation information associated with the integrated microsensors in the guidewire to efficiently navigate the guidewire to a desired location within a body.

It is very difficult to incorporate trackable microsensors of high signal strength into devices of the sizes provided by typical guidewires having a diameter of less than a 1 mm. Additionally, trackable microsensors may require a shielded type of electrical connection (e.g., coax or twisted pair) with the surgical navigation tracking system to reduce the introduction of noise into the tracking signals. The microsensors must efficiently occupy the volume available to maximize signal strength without affecting the clinical and mechanical performance of the guidewire. The guidewire must be robust for the clinical applications contemplated and the trackable microsensors must have minimal impact on the mechanical performance of the guidewire, especially with regards to pushability and steerability.

Therefore, it is desirable to provide a guidewire with the ability of coupling at least one trackable device into the guidewire for systematically navigating the guidewire to a desired location within a body and having minimal impact on the performance of the guidewire during clinical applications.

BRIEF DESCRIPTION OF THE INVENTION

In accordance with an aspect of the disclosure, a guidewire assembly comprising a substantially flexible flat member having a plurality of projections extending therefrom; and at least one electromagnetic microsensor attached to each of the plurality of projections; wherein the substantially flexible flat member with the at least one electromagnetic microsensor attached to each of the plurality of projections is wound around a mandrel to form a spring-like flexible tip member.

In accordance with an aspect of the disclosure, a guidewire assembly comprising a substantially tubular member having a plurality of projections extending outwardly therefrom and a plurality of openings extending therethrough; and at least one electromagnetic microsensor attached to each of the plurality of projections; wherein the at least one electromagnetic microsensor attached to each of the plurality of projections are positioned within the tubular member to form a flexible tip member.

In accordance with an aspect of the disclosure, a method for making a trackable guidewire assembly comprising providing a substantially flexible flat member having a plurality of projections extending therefrom; attaching at least one electromagnetic microsensor to each of the plurality of projections; winding the substantially flexible flat member with the electromagnetic microsensors attached thereto around a mandrel to create a flexible tip member; and attaching a strengthening member to a proximal end of the flexible tip member to create a guidewire assembly.

In accordance with an aspect of the disclosure, a method for making a trackable guidewire assembly comprising providing a substantially tubular member having a plurality of projections extending outwardly therefrom and a plurality of openings extending therefrom; attaching at least one electromagnetic microsensor to each of the plurality of projections; positioning the plurality of projections with the electromagnetic microsensors attached thereto within the substantially tubular member to create a flexible tip member; and attaching a strengthening member to a proximal end of the flexible tip member to create a guidewire assembly.

Various other features, aspects, and advantages will be made apparent to those skilled in the art from the accompanying drawings and detailed description thereof.

BRIEF DESCRIPTION OF THE DRAWINGS

FIG. 1 is a top view of an exemplary embodiment of a portion of a substantially flexible flat member with a plurality of projections extending outwardly at an angle from one side thereof;

FIG. 2 is a top view of the substantially flexible flat member of FIG. 1 with the plurality of projections extending substantially perpendicular with respect to the substantially flexible flat member;

DETAILED DESCRIPTION OF THE INVENTION

Figure 3:
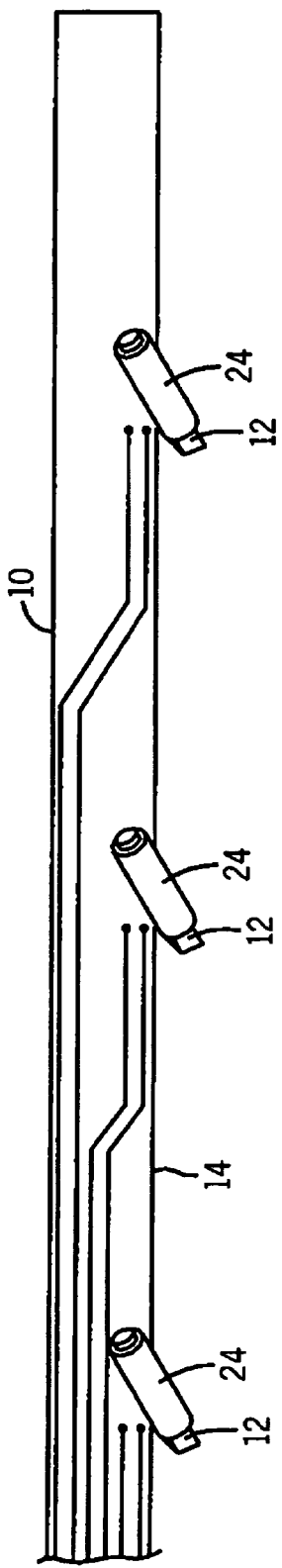
FIG. 3 is a top view of the substantially flexible flat member of FIG. 2 with at least one electromagnetic microsensor attached to each of the plurality of projections.

Referring to the drawings, FIGS. 1-9 illustrate a structure and method of forming a spring-like flexible tip member 40 for a trackable guidewire assembly 60 made out of a substantially flexible flat member 10 that may be formed into the spring-like flexible tip member 40 with a plurality of electromagnetic microsensors 24 incorporated into the center of the spring-like flexible tip member 40 to function as the spring-like flexible tip member 40 of the guidewire assembly 60.

FIG. 1 illustrates a top view of an exemplary embodiment of a portion of a substantially flexible flat member 10 with a plurality of projections 12 extending outwardly at an angle from one side 14 thereof for use in making a flexible tip for a guidewire. The substantially flexible flat member 10 may be cut from a stock of flat flexible material. The substantially flexible flat member 10 may be made up of a flat flexible material that may be easily formed into a spring-like structure. In an exemplary embodiment, the substantially flexible flat member 10 may comprise materials selected from the group of stainless steel, nickel, titanium, alloys of these materials, e.g., nickel-titanium alloy (nitonal), plastics, and composite materials.

In an exemplary embodiment, the substantially flexible flat member 11 may be 2 to 3 meters long that tapers to an end at one end thereof. In an exemplary embodiment, the angle at which each of the plurality of projections 12 extends from one side 14 of the substantially flexible flat member 10 may be any angle from approximately 20 to 70 degrees.

The substantially flexible flat member 10 includes at least two plated electrical feedthrough contacts 16 located at a base 20 of each projection 12 with a plated electrical conductor lead or trace 18 extending from one side of each feedthrough contact 16 along the length of the substantially flexible flat member 10 for connection to an electromagnetic microsensor that is attached to each projection 12.

In an exemplary embodiment, the feedthrough contacts 16 and traces 18 comprise conductive material such as copper, silver, gold, or any other conductive material. The feedthrough contacts 16 are designed for connection to electrical components, such as electromagnetic microsensors. The traces 18 are designed for transmitting or receiving electrical power or electronic signals from the feedthrough contacts 16 to what ever is connected to the end of the traces 18 at the end of the substantially flexible flat member 10. In an exemplary embodiment, there may be additional feedthrough contacts at the end of the traces 18 at opposite end of the substantially flexible flat member 10, opposite the feedthrough contacts 16.

In preparation for attachment of an electromagnetic microsensor to each of the plurality of projections 12 of the substantially flexible flat member 10, each of the projections 12 are bent upwardly at their base 20 so that they are substantially perpendicular to a horizontal plane 22 of the substantially flexible flat member 10. FIG. 2 illustrates a top view of the substantially flexible flat member 10 with the plurality of projections 12 extending substantially perpendicular with respect to the horizontal plane 22 of the substantially flexible flat member 10.

FIG. 3 illustrates the substantially flexible flat member 10 with at least one electromagnetic microsensor 24 attached to each of the plurality of projections 12. In an exemplary embodiment, the electromagnetic microsensor 24 may be built with various electromagnetic microsensor architectures, including, but not limited to electromagnetic microcoils, flux gate magnetometer sensors, squid magnetometer sensors, Hall-effect sensors, anisotropic magneto-resistance (AMR) sensors, giant magneto-resistance (GMR) sensors, and extraordinary magneto-resistance (EMR) sensors.

In an exemplary embodiment, the electromagnetic microsensor 24 may be an electromagnetic microcoil that may be built with various electromagnetic microcoil architectures. In an exemplary embodiment, the electromagnetic microsensor 24 may include a ferrite core with wire wound around the ferrite core. In an exemplary embodiment, the electromagnetic microsensor 24 may include a ferrite material, such as a ferrite paste, that is applied to each of the plurality of projections 12 with wire wound around the ferrite material. In an exemplary embodiment, each electromagnetic microsensor 24 may be sealed within a shrink wrap sleeve or coating on the outside of the microsensor 24 with a shrinkable material.

Figure 4:
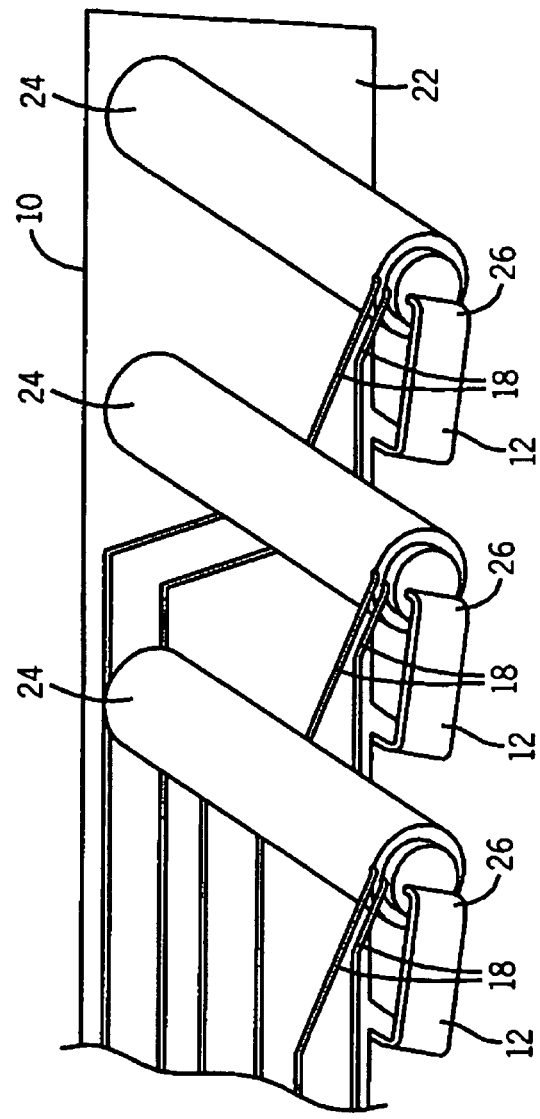
FIG. 4 is a top view of a portion of the substantially flexible flat member of FIG. 3 with the plurality of projections with the at least one electromagnetic microsensor attached thereto extending substantially parallel to and spaced apart from the substantially flexible flat member.

In preparation for winding the substantially flexible flat member 10 around a mandrel 30 for making a spring-like flexible tip member for a guidewire, each of the plurality of projections 12 with the at least one electromagnetic microsensor 24 attached thereto are bent downwardly at the bottom 26 of the electromagnetic microsensor 24 so that the plurality of projections 12 with the at least one electromagnetic microsensor 24 attached thereto are substantially parallel to the horizontal plane 22 of the substantially flexible flat member 10. FIG. 4 illustrates a top view of a portion of the substantially flexible flat member 10 with the plurality of projections 12 with the at least one electromagnetic microsensor 24 attached to each of the plurality of projections 12 extending substantially parallel to and spaced apart from the substantially flexible flat member 10.

In an exemplary embodiment, each of the electromagnetic microsensors 24 include fine electrical conductor leads or conductors 28 that are brazed, soldered, or welded to the feedthrough contacts 16. In an exemplary embodiment, having three electromagnetic microsensors 24, there may be six traces, three traces, two traces or one trace. The electromagnetic microsensors 24 may each include at least one electrical return. The electrical return from each electromagnetic microsensor 24 may be combined together. In an exemplary embodiment, the electrical return from the electromagnetic microsensor 24 may be the substantially flexible flat member 10. In this embodiment, the substantially flexible flat member 10 must be treated to be isolated from traces. In an exemplary embodiment, the electrical return from an electromagnetic microcoil may be the microcoil itself.

Figure 5:
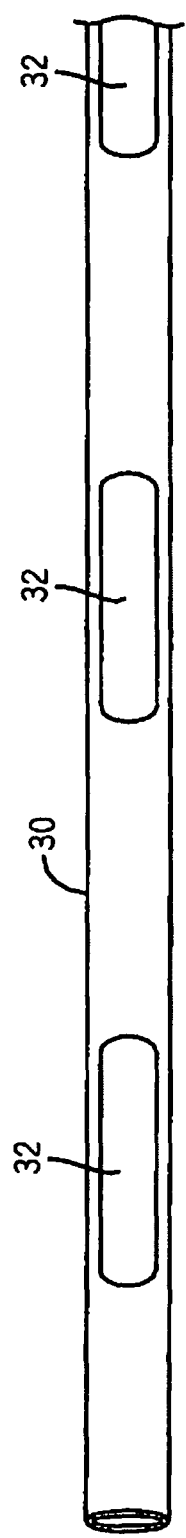
FIG. 5 is a perspective view of a portion of an exemplary embodiment of a mandrel used for making a flexible tip for a guidewire out of the substantially flexible flat member with the plurality of electromagnetic microsensors attached thereto.

FIG. 5 illustrates a perspective view of a portion of an exemplary embodiment of a mandrel 30 used for making a spring-like flexible tip member 40 for a guidewire out of the substantially flexible flat member 10 with the plurality of electromagnetic microsensors 24 attached thereto. In an exemplary embodiment, the mandrel 30 is a hollow cylindrical rod around which the substantially flexible flat member 10 may be wound for forming the spring-like flexible tip member 40 for a guidewire. The mandrel 30 includes a plurality of openings 32 extending thereto for accepting the plurality of electromagnetic microsensors 24 therein. The openings 32 should be large enough to clearly accept the electromagnetic microsensors 24 therein. The substantially flexible flat member 10 is wound around the mandrel 30 to form a spring-like flexible tip member 40 for a guidewire with a plurality of electromagnetic microsensors 24 positioned within the center of the spring-like flexible tip member 40, as shown in FIG. 6.

Figure 6:
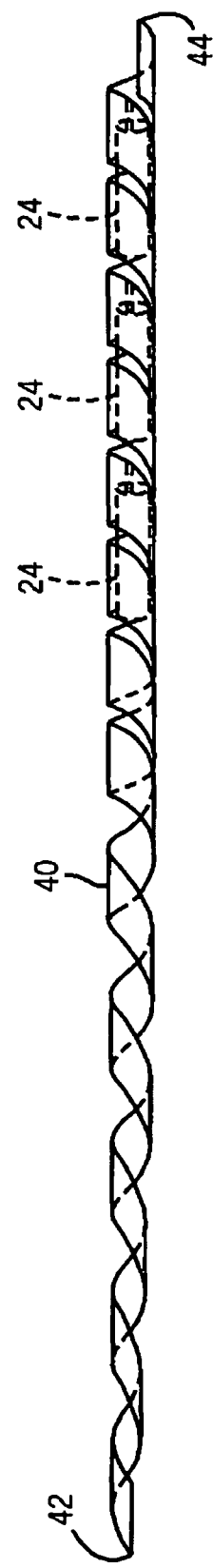
FIG. 6 is a perspective view of an exemplary embodiment of a spring-like flexible tip member for a guidewire after winding the substantially flexible flat member around the mandrel.

FIG. 6 illustrates a perspective view of an exemplary embodiment of a spring-like flexible tip member 40 for a guidewire after winding the substantially flexible flat member 10 around the mandrel 30. The spring-like flexible tip member 40 includes a distal end 42 and a proximate end 44. The spring-like flexible tip member 40 further includes the plurality of electromagnetic microsensors 24 that are attached to and positioned within the center of the spring-like flexible tip member 40. Each of the electromagnetic microsensors 24 include at least one electrical signal line and an electrical return that extend from the plurality of electromagnetic microsensors 24 through the feedthrough contacts 16 and traces 18 to the end of the guidewire.

In an exemplary embodiment, the mandrel 30 may be left inside the spring-like flexible tip member 40 to function as a guidewire core or may be removed from the spring-like flexible tip member 40 after winding. In an exemplary embodiment, the spring-like flexible tip member 40 may be a relatively short distal portion of the guidewire or continue to the proximal end with a guidewire core inside the spring-like flexible tip member 40.

In an exemplary embodiment, the spring-like flexible tip member 40 may be laser cut from a hollow cylindrical tube of material having a plurality of electromagnetic microsensors 24 that are attached to and positioned within the center of the spring-like flexible tip member 40.

Figure 7:
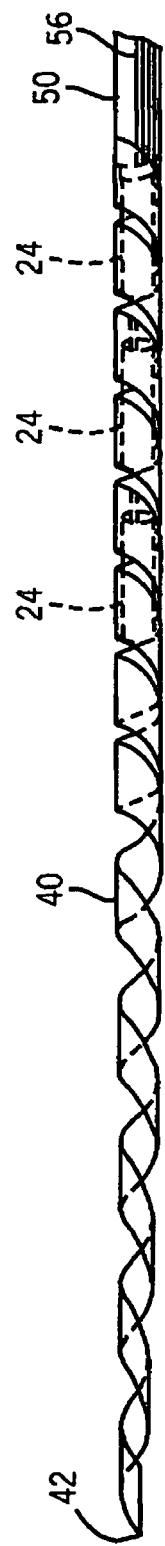
FIG. 7 is a perspective view of an exemplary embodiment of the spring-like flexible tip member of FIG. 6 attached to a strengthening member of a guidewire.
Figure 8:
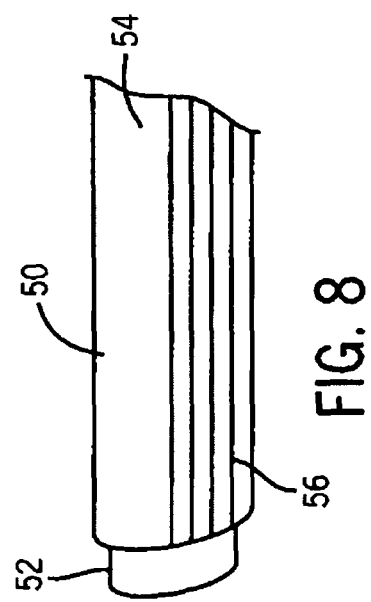
FIG. 8 is an enlarged perspective view of a distal end of the strengthening member of the guidewire of FIG. 7.

FIG. 7 illustrates a perspective view of an exemplary embodiment of the spring-like flexible tip member 40 of FIG. 6 attached to a strengthening member 50 of a guidewire. FIG. 8 illustrates an enlarged perspective view of the distal end 52 of the strengthening member 50 of the guidewire. The strengthening member 50 may be a solid wire or a hollow cylindrical tube with a plurality of plated electrical conductor leads or traces 56 extending along the length of the strengthening member 50 of the guidewire. The strengthening member 50 includes a distal end 52 and a proximal end 54. The distal end 52 of the strengthening member 50 may be brazed, soldered, or welded to the proximal end 44 of the spring-like flexible tip member 40. In an exemplary embodiment, strengthening member 50 may comprise materials selected from the group of stainless steel, nickel, titanium, alloys of these materials, e.g., nickel-titanium alloy (nitonal), plastics, and composite materials.

Figure 9:
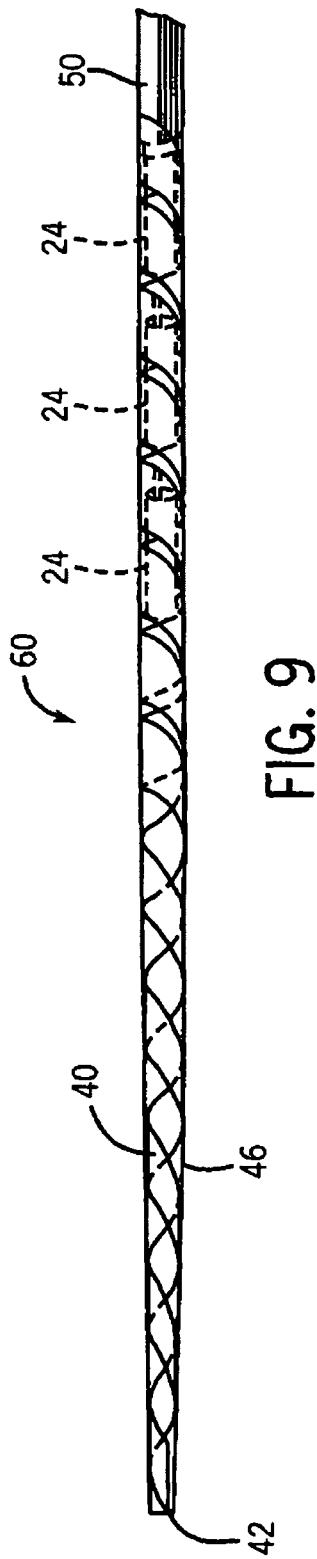
FIG. 9 is a perspective view of a portion of an exemplary embodiment of a guidewire assembly.

FIG. 9 illustrates a perspective view of a portion of an exemplary embodiment of a guidewire assembly 60. In an exemplary embodiment, the spring-like flexible tip member 40 may be sealed within an outer member 46 forming an outer covering around the outside of the spring-like flexible tip member 40 or around the outside of the guidewire assembly 60 with a shrinkable protective material.

Figure 10:
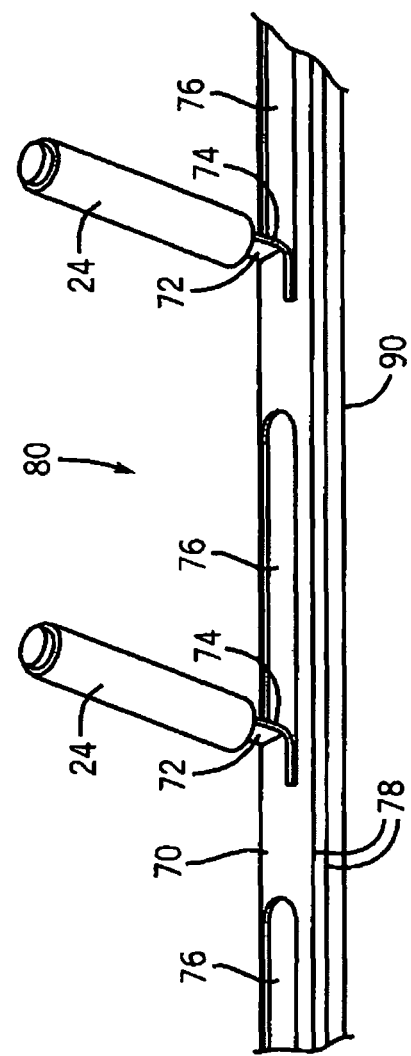
FIG. 10 is a perspective view of a tip portion of a guidewire with at least one electromagnetic microsensor attached to each of a plurality of projections of the tip portion.
Figure 11:
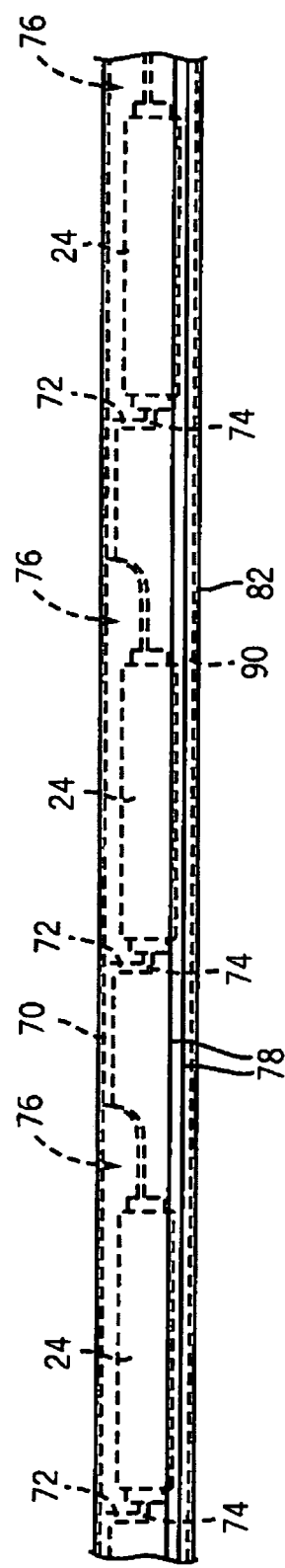
FIG. 11 is a perspective view of the tip portion of the guidewire of FIG. 10 with the plurality of electromagnetic microsensors positioned within the center of the tip portion.

FIGS. 10 and 11 illustrate a flexible tip member 70 for a trackable guidewire assembly 80 made out of a substantially tubular member 90 with a plurality of electromagnetic microsensors 24 incorporated into the center of the substantially tubular member 90 to function as the flexible tip member 70 of the guidewire assembly 80.

FIG. 10 illustrates a perspective view of an exemplary embodiment of a flexible tip member 70 of a guidewire assembly 80 with at least one electromagnetic microsensor 24 attached to each of a plurality of projections 72 of the flexible tip member 70. The flexible tip member 70 is made from a substantially tubular member 90 with a plurality of projections 72 attached to and extending upwardly from the substantially tubular member 90 at one end 74 thereof. The substantially tubular member 90 farther includes a plurality of openings 76 extending therethrough and positioned adjacent to the end 74 of the plurality of projections 72 that is attached to the substantially tubular member 90 for accepting the plurality of electromagnetic microsensors 24 therein. The openings 76 should be large enough to clearly accept the electromagnetic microsensors 24 therein.

The substantially tubular member 90 further includes a plurality of plated electrical conductor leads or traces 78 extending along the length of the substantially tubular member 90 for connection to the at least one electromagnetic microsensor 24 attached to each of the plurality of projections 72.

In an exemplary embodiment, the traces 78 comprise conductive material such as copper, silver, gold, or any other conductive material. The traces 78 are designed for transmitting or receiving electrical power or electronic signals from the plurality of electromagnetic microsensors 24 to what ever is connected to the end of the traces 78 at the end of the substantially tubular member 90. Each of the electromagnetic microsensors 24 include at least one electrical signal line and an electrical return that are coupled to the traces 78 that extend along the length of the guidewire assembly 80.

In an exemplary embodiment, the electromagnetic microsensors 24 may be built with various electromagnetic microsensor architectures, including, but not limited to electromagnetic microcoils, flux gate magnetometer sensors, squid magnetometer sensors, Hall-effect sensors, anisotropic magneto-resistance (AMR) sensors, giant magneto-resistance (GMR) sensors, and extraordinary magneto-resistance (EMR) sensors.

In an exemplary embodiment, the electromagnetic microsensors 24 may be electromagnetic microcoils that may be built with various electromagnetic microcoil architectures. In an exemplary embodiment, the electromagnetic microsensors 24 may each include a ferrite core with wire wound around the ferrite core. In an exemplary embodiment, the electromagnetic microsensors 24 may each include a ferrite material, such as a ferrite paste, that is applied to each of the plurality of projections 72 with wire wound around the ferrite material. In an exemplary embodiment, each electromagnetic microsensor 24 may be sealed within a shrink wrap sleeve or coating on the outside of the microsensor 24 with a shrinkable material.

In an exemplary embodiment, the substantially tubular member 90 may comprise materials selected from the group of stainless steel, nickel, titanium, alloys of these materials, e.g., nickel-titanium alloy (nitonal), plastics, and composite materials.

FIG. 11 illustrates a perspective view of the flexible tip member 70 of the guidewire assembly 80 of FIG. 10 with the plurality of electromagnetic microsensors 24 positioned within the center of the flexible tip member 70. The plurality of projections 72 with the at least one electromagnetic microsensor attached thereto are pushed inside of the flexible tip member 70, such that the plurality of electromagnetic microsensors 24 positioned within the center of the substantially tubular member 90.

In an exemplary embodiment, the flexible tip member 70 may be sealed within an outer member 82 forming an outer covering around the outside of the flexible tip member 70 or around the outside of the guidewire assembly 80 with a shrinkable protective material.

Figure 12:
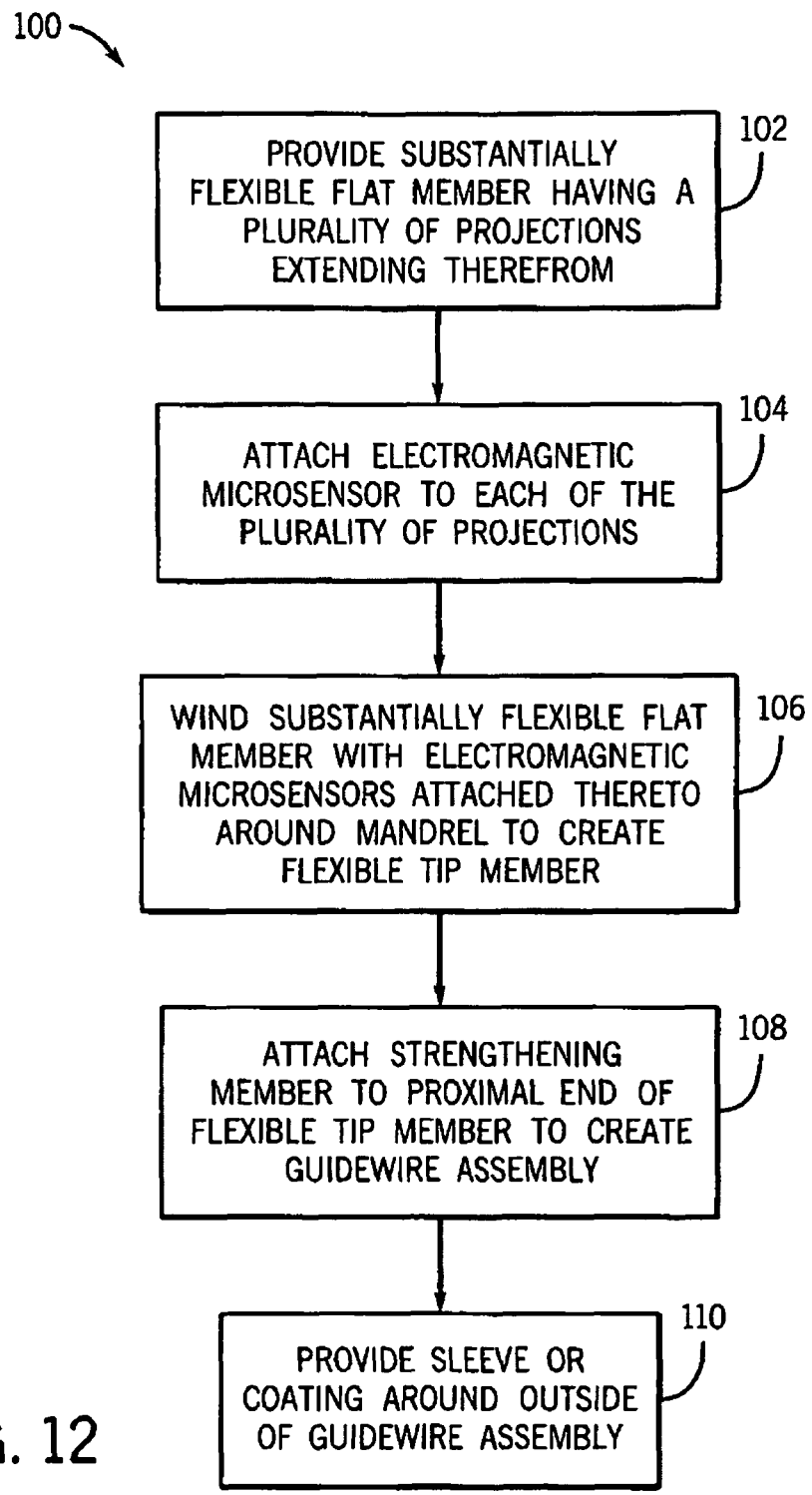
FIG. 12 is a flow diagram of an exemplary embodiment of a method for making a trackable guidewire assembly.

FIG. 12 illustrates a flow diagram of an exemplary embodiment of a method 100 for making a trackable guidewire assembly. The method 100 includes providing a substantially flexible flat member having a plurality of projections extending therefrom 102. Another step in the method is attaching at least one electromagnetic microsensor to each of the plurality of projections 104. The electromagnetic microsensors are properly positioned relative to the substantially flexible flat member for winding the substantially flexible flat member on a mandrel. This step includes winding the substantially flexible flat member with the electromagnetic microsensors attached thereto around the mandrel to create a spring-like flexible tip member for a guidewire 106. The next step is attaching a strengthening member to a proximal end of the spring-like flexible tip member to create a guidewire assembly 108. A sleeve or coating may be provided around the outside of the spring-like flexible tip member or the entire guidewire assembly 110.

Figure 13:
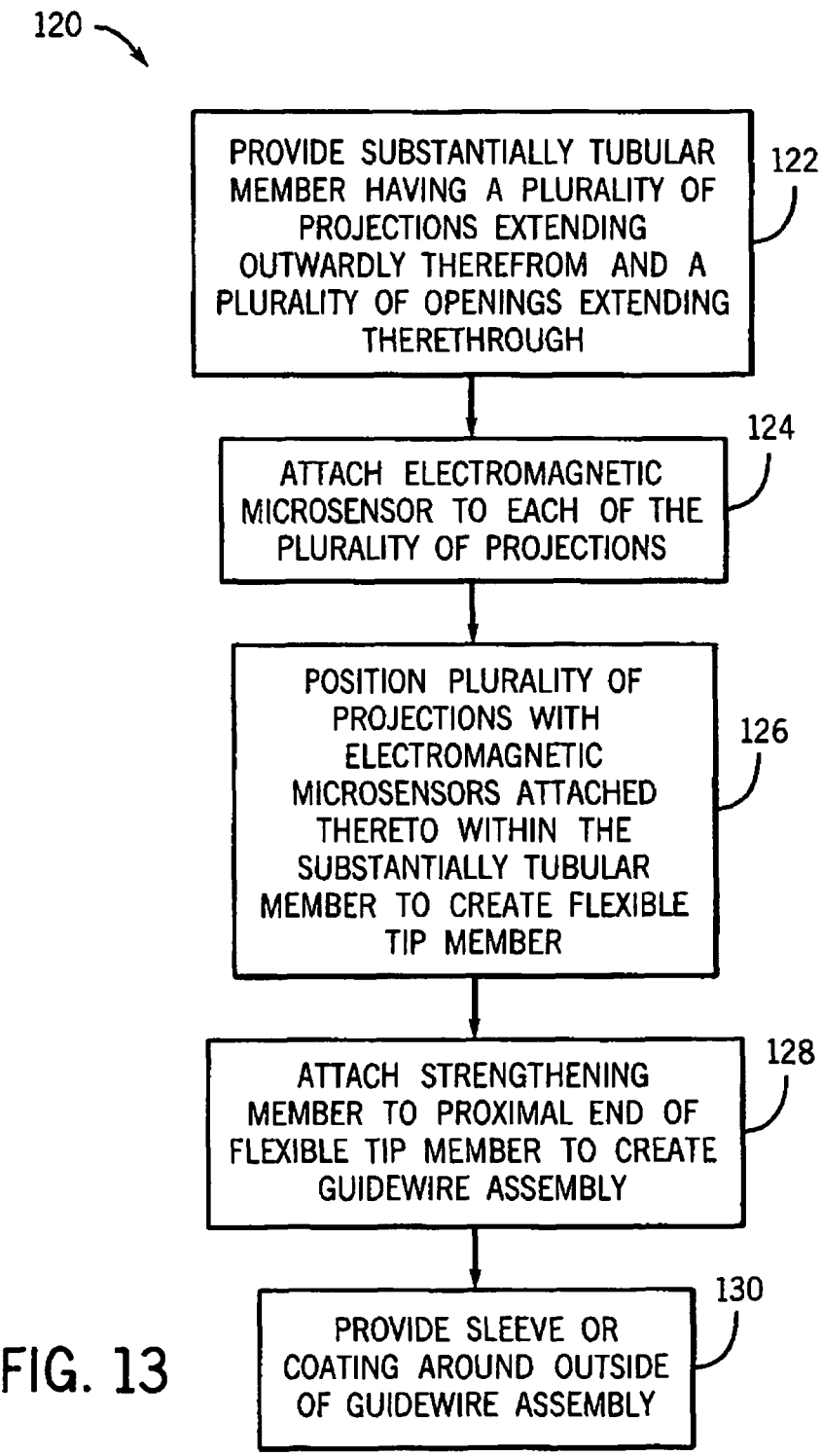
FIG. 13 is a flow diagram of an exemplary embodiment of a method for making a trackable guidewire assembly.

FIG. 13 illustrates a flow diagram of an exemplary embodiment of a method 120 for making a trackable guidewire assembly. The method 120 includes providing a substantially tubular member having a plurality of projections extending outwardly therefrom and a plurality of openings extending therethrough for accepting a plurality electromagnetic microsensors therein 122. Another step in the method is attaching at least one electromagnetic microsensor to each of the plurality of projections 124. The plurality of projections with electromagnetic microsensors attached thereto within the substantially tubular member to create a flexible tip member for a guidewire 126. The next step is attaching a strengthening member to a proximal end of the flexible tip member to create a guidewire assembly 128. A sleeve or coating may be provided around the outside of the flexible tip member or the entire guidewire assembly 130.

Several embodiments are described above with reference to drawings. These drawings illustrate certain details of exemplary embodiments that implement the apparatus, assemblies, systems, and methods of this disclosure. However, the drawings should not be construed as imposing any limitations associated with features shown in the drawings.

The exemplary embodiments described herein provide specific, feasible apparatus, systems, and methods of integrating electromagnetically trackable microsensors into guidewires that do not currently exist. By integrating microsensors into guidewires in a robust and clinically effective way, minimally invasive surgical techniques and interventional procedures, can utilize electromagnetic tracking technology to provide more efficient treatments, less radiation dose, and faster procedures.

The exemplary embodiments of guidewires described herein may be used as part of a surgical navigation system employing electromagnetic tracking technology that may be used in an interventional surgical suite. The surgical navigation system may be integrated into a fixed C-arm system, a portable C-arm system, or a stand-alone tracking (electromagnetic-based navigation) system.

The foregoing description of exemplary embodiments has been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and its practical application to enable one skilled in the art to utilize the invention in various embodiments and with various modifications as are suited to the particular use contemplated.

While the disclosure has been described with reference to various embodiments, those skilled in the art will appreciate that certain substitutions, alterations and omissions may be made to the embodiments without departing from the spirit of the disclosure. Accordingly, the foregoing description is meant to be exemplary only, and should not limit the scope of the disclosure as set forth in the following claims.

What is claimed is:

1. A guidewire assembly, comprising:
   a substantially flexible flat member having been wound into coils to form a spring-like flexible tip member having a side and an end;
   a plurality of projections separated and bent away from the side of the flat member so that they extend in a direction different from the direction in which the coils are wound; and
   at least one electromagnetic microsensor attached to each of the plurality of projections, wherein the at least one electromagnetic microsensor comprises an electromagnetic microcoil with a ferrite core and wire wound around the ferrite core.

2. The guidewire assembly of claim 1, wherein the plurality of projections extend along one side of the substantially flexible flat member.

3. The guidewire assembly of claim 2, wherein the plurality of projections extend at an angle from one side of the substantially flexible flat member.

4. The guidewire assembly of claim 1, further comprising at least one electrically conductive trace extending from each of the plurality of projections at an electrically conductive feedthrough contact along the length of the substantially flexible flat member for coupling to the at least one electromagnetic microsensor.

5. The guidewire assembly of claim 1, further comprising a strengthening member attached to a proximal end of the spring-like flexible tip member.

6. The guidewire assembly of claim 5, wherein the strengthening member includes a plurality of electrically conductive traces coupled to electrically conductive traces extending from each of the plurality of projections along the length of the substantially flexible flat member.

7. The guidewire assembly of claim 1, wherein each of the plurality of projections is bent so as to run substantially parallel to a horizontal plane of the spring-like flexible tip member.

8. The guidewire assembly of claim 1, further comprising an outer member forming an outer covering around the guidewire.

9. The guidewire assembly of claim 1, wherein the plurality of projections extend within the center of the coils.

10. The guidewire assembly of claim 1, wherein the substantially flexible flat member tapers to an end thereof.

11. The guidewire assembly of claim 1, wherein each of the plurality of projections extending from the substantially flexible flat member terminates at its own separate end.

12. The guidewire assembly of claim 1, wherein the substantially flexible flat member and each of the plurality of projections are formed from a single piece of material.

13. The guidewire assembly of claim 1, wherein a mandrel is left inside of the spring-like tip member.

14. The guidewire assembly of claim 1, wherein the electromagnetic microsensor is attached around each of the plurality of projections.

15. A guidewire assembly, comprising:
a substantially flexible flat member having been wound into coils to form a spring-like flexible tip member having a side and an end, the spring-like tip member containing a mandrel therein;
a plurality of projections separated and bent away from the side of the flat member so that they extend in a direction different from the direction in which the coils are wound; and
at least one electromagnetic microsensor attached to each of the plurality of projections.

16. The guidewire assembly of claim 15, wherein the plurality of projections extend along one side of the substantially flexible flat member.

17. The guidewire assembly of claim 16, wherein the plurality of projections extend at an angle from one side of the substantially flexible flat member.

18. The guidewire assembly of claim 15, further comprising at least one electrically conductive trace extending from each of the plurality of projections at an electrically conductive feedthrough contact along the length of the substantially flexible flat member for coupling to the at least one electromagnetic microsensor.

19. The guidewire assembly of claim 15, further comprising a strengthening member attached to a proximal end of the spring-like flexible tip member.

20. The guidewire assembly of claim 19, wherein the strengthening member includes a plurality of electrically conductive traces coupled to electrically conductive traces extending from each of the plurality of projections along the length of the substantially flexible flat member.

21. The guidewire assembly of claim 15, wherein each of the plurality of projections is bent so as to run substantially parallel to a horizontal plane of the spring-like flexible tip member.

22. The guidewire assembly of claim 15, further comprising an outer member forming an outer covering around the guidewire.

23. The guidewire assembly of claim 15, wherein the at least one electromagnetic microsensor comprises an electromagnetic microcoil with a ferrite core and wire wound around the ferrite core.

24. The guidewire assembly of claim 15, wherein the plurality of projections extend within the center of the coils.

25. The guidewire assembly of claim 15, wherein the substantially flexible flat member tapers to an end thereof.

26. The guidewire assembly of claim 15, wherein each of the plurality of projections extending from the substantially flexible flat member terminates at its own separate end.

27. The guidewire assembly of claim 15, wherein the substantially flexible flat member and each of the plurality of projections are formed from a single piece of material.

28. The guidewire assembly of claim 15, wherein the electromagnetic microsensor is attached around each of the plurality of projections.

* * * * *

UNITED STATES PATENT AND TRADEMARK OFFICE
CERTIFICATE OF CORRECTION

PATENT NO. : 9,002,435 B2
APPLICATION NO. : 12/165636
DATED : April 7, 2015
INVENTOR(S) : Ella Zaslavsky and Samuel Joseph Akins Page 1 of 1

It is certified that error appears in the above-identified patent and that said Letters Patent is hereby corrected as shown below:

Specification

In Column 2, line 5, please delete "thereform" and replace with --therefrom--.
In Column 3, line 44, please delete "nitonal" and replace with --nitinol--.
In Column 3, line 47, please delete "11" and replace with --10--.
In Column 4, line 2, please insert --16-- between contact and at.
In Column 4, line 36, please insert --electromagnetic-- between the and microsensor.
In Column 5, line 59, please delete "nitonal" and replace with --nitinol--.
In Column 6, line 62, please delete "nitonal" and replace with --nitinol--.

Signed and Sealed this
Ninth Day of February, 2016

Michelle K. Lee
*Director of the United States Patent and Trademark Office*